United States Patent
Decaux et al.

(10) Patent No.: US 9,745,612 B2
(45) Date of Patent: Aug. 29, 2017

(54) OPTICAL METHOD FOR CONTROLLING THE MOVEMENT OF A SAMPLING TOOL

(71) Applicant: bioMérieux, Marcy-l'Etoile (FR)

(72) Inventors: Dominique Decaux, Chaponost (FR); Régis Montvernay, Lyons (FR); Frédéric Pinston, Grenoble (FR)

(73) Assignee: bioMérieux, Marcy l'Etoile (FR)

( * ) Notice: Subject to any disclaimer, the term of this patent is extended or adjusted under 35 U.S.C. 154(b) by 95 days.

(21) Appl. No.: 14/357,147

(22) PCT Filed: Nov. 16, 2012

(86) PCT No.: PCT/FR2012/052655
§ 371 (c)(1),
(2) Date: May 8, 2014

(87) PCT Pub. No.: WO2013/072643
PCT Pub. Date: May 23, 2013

(65) Prior Publication Data
US 2014/0322745 A1    Oct. 30, 2014

(30) Foreign Application Priority Data
Nov. 17, 2011 (FR) ...................................... 11 60497

(51) Int. Cl.
| | |
|---|---|
| C12Q 1/24 | (2006.01) |
| G01N 35/10 | (2006.01) |
| G05B 19/19 | (2006.01) |
| G05B 19/402 | (2006.01) |
| C12M 1/30 | (2006.01) |
| C12M 1/26 | (2006.01) |

(52) U.S. Cl.
CPC ............... *C12Q 1/24* (2013.01); *C12M 33/02* (2013.01); *C12M 33/04* (2013.01); *G01N 35/1011* (2013.01); *G05B 19/19* (2013.01); *G05B 19/402* (2013.01)

(58) Field of Classification Search
None
See application file for complete search history.

(56) References Cited

U.S. PATENT DOCUMENTS

| | | | |
|---|---|---|---|
| 4,627,009 A * | 12/1986 | Holmes | ................... H01J 37/20 250/442.11 |
| 4,818,491 A | 4/1989 | Fariss | |
| 4,846,003 A | 7/1989 | Marquiss | |
| 5,723,795 A | 3/1998 | Merriam | |
| 7,009,177 B1 * | 3/2006 | Mankos | ............. H01J 37/1478 250/307 |
| 7,881,533 B2 | 2/2011 | Ando et al. | |
| 2005/0007135 A1 | 1/2005 | Schneidewind et al. | |
| 2006/0043287 A1 | 3/2006 | Munekane | |
| 2008/0126051 A1 | 5/2008 | Ando et al. | |

FOREIGN PATENT DOCUMENTS

| | | |
|---|---|---|
| DE | 102004030881 A1 | 4/2005 |
| EP | 0341438 A2 | 11/1989 |
| EP | 0571100 A1 | 11/1993 |
| JP | 2002171995 A | 6/2002 |
| JP | 2006093102 A | 4/2006 |

OTHER PUBLICATIONS

Definition of "project", Dictionary.com, accessed Jan. 18, 2017 at http://www.dictionary.com/browse/project?s=t.*
Dörre, Thorsten, "International Search Report," prepared for PCT/FR2012/052655, as mailed May 24, 2013, three pages.

* cited by examiner

*Primary Examiner* — Robert Yamasaki
(74) *Attorney, Agent, or Firm* — Winstead PC (57) ABSTRACT

The present invention relates to a method of sampling biological material on a reference surface, such as the surface of an agar medium, with the aid of a sampling tool, said method making it possible to steer the displacement of the sampling tool towards the reference surface, from a first position towards a second position, and/or of the reference surface towards the sampling tool, from a first position towards a second position, said second position being a contact position in which the sampling tool and the reference surface are in contact, said method comprising the following steps:

a) illuminating the sampling tool in said first position in order to make the sampling tool visible and to project an image of the sampling tool onto the reference surface, b) acquiring an image of both the sampling tool and its image projected onto the reference surface, c) processing the image obtained in step b) in order to determine if, on the processed image, the gap between the sampling tool and its projected image is equal to zero, d) if the gap between the sampling tool and its projected image is not equal to zero.

15 Claims, 4 Drawing Sheets

OPTICAL METHOD FOR CONTROLLING THE MOVEMENT OF A SAMPLING TOOL

The invention relates to a method of steering the displacement of a sampling tool towards a reference surface and/or of a reference surface towards a sampling tool, a device for implementing this method, as well as a biological material sampling apparatus comprising said device.

In other words, the method according to the present invention makes it possible to steer the displacement of a biological material sampling tool, such as a pipette, in the direction of a reference surface. Said reference surface may in particular consist of a Petri dish filled with agar on which the biological material of interest is cultured.

"Biological material" is understood to be any material containing genetic data and which is self-propagating in a biological system. As such, in particular any bacterial or viral cell cultures may be cited.

There are a number of solutions for sampling biological material, such as a bacterial colony cultured on a Petri dish, with a view to carrying out subsequent analyses.

This sampling of biological material may in particular be carried out by means of "passive" sampling tools, for example a tool equipped on its end with a cotton element intended to come into contact with a bacterial colony. Alternatively, "active" sampling tools are used, such as for example pipettes using the suction/discharge principle. These sampling tools may be manual or automated.

In order not to distort the analysis of the sampled biological material, it is important to sample only the biological material of interest whilst refraining from sampling any substance which is foreign to the latter, such as substances which come from the culture medium per se. This foreign substance may be termed a contaminating substance. Regarding bacterial sampling on a Petri dish, it is therefore advisable to avoid sampling the agar at the same time as the biological material of interest.

In fact, unintentionally sampled agar may disrupt both the quantitative and qualitative analysis of the sampled biological material.

Regarding quantitative analysis, agar medium residues may distort the measurement of the optical density of a sample containing the bacterial suspension by artificially opacifying this bacterial suspension.

With regard to qualitative analysis, for example analysis by mass spectrometry, the agar residues will induce the detection of compounds which are foreign to the biological material of interest, which generates a background noise disrupting the analysis.

Furthermore, it is possible for a contaminating bacterial colony to proliferate under a bacterial colony of interest. In this scenario, it is important, when sampling the bacterial colony of interest, not to sample the contaminating bacteria so as not to distort the corresponding analysis.

Several devices have been developed in the prior art, in order to attempt to avoid such contamination phenomena due primarily to the sampling tool penetrating too far into the solid, liquid or semi-solid culture medium, for example the tip of a pipette penetrating into the agar.

A first type of device from the prior art makes it possible to detect the contact of the sampling tool with a surface using capacitive properties, by electrical contact.

Firstly, there is the case of the non-disposable metal needle which functions as an electrode, the second electrode being the liquid into which the needle will dip. When this needle comes into contact with the biological sample, a variation in impedance, capacitance or resistance, after amplification, triggers the stopping of the needle-lowering motor. The devices and methods using this technique are in particular described in document U.S. Pat. No. 4,818,491.

Secondly, a plug-in conductive cone or tip, and which is therefore disposable after each sampling by the pipette associated with the cone. The latter is made from a carbon particle-filled plastic material, and the electrical connection is ensured by the cone gripper which must be conductive.

Thirdly, other systems work by adding to the sampling needle or sampling cone two electrodes flanked either side of the needle or cone, and ensuring the electrical conductivity when these electrodes come into contact with the biological liquid. The latter variant presents the major flaw of contaminating the electrodes each time they come into contact with a new biological liquid, which in this case necessitates the addition of a decontaminating washing system.

However, this first type of device from the prior art using capacitive properties necessitates electrically conductive tools.

A second type of device from the prior art which makes it possible to detect the contact of the sampling tool and a surface uses acoustic methods. Thus, U.S. Pat. No. 4,846,003 describes a detection system which uses an acoustic characteristic emitted by a speaker and received by a microphone. The measured value is constituted by the acoustic impedance.

A third type of device from the prior art uses pressure sensors (see EP-A-0.341.438, U.S. Pat. No. 5,723,795 and EP-A-0.571100). More precisely, a pressure variation is detected once the free end of the tip comes into contact with the surface of a liquid.

Finally, a final device from the prior art concerns the detection of a surface by ultrasound. This technique is however not suitable for small elements such as bacterial colonies.

However, none of the above-mentioned devices from the prior art makes it possible to obtain a "universal" means of controlling the displacement of a sampling tool towards a reference surface and/or of a reference surface towards a sampling tool that can be used whatever the type of sampling tool employed and whatever the nature or consistency of said reference surface, whilst still ensuring effective control of the displacement of the sampling tool towards the reference surface and/or of the reference surface towards the sampling tool.

Thus, the object of the present invention is a method of sampling biological material on a reference surface, such as the surface of an agar medium, with the aid of a sampling tool, said method making it possible to steer the displacement of the sampling tool towards the reference surface, from a first position towards a second position, and/or of the reference surface towards the sampling tool, from a first position towards a second position, said second position being a contact position in which the sampling tool and the reference surface are in contact, said method comprising the following steps:

a) illuminating the sampling tool in said first position in order to make the sampling tool visible and to project an image of the sampling tool onto the reference surface, b) acquiring an image of both the sampling tool and its image projected onto the reference surface, c) processing the image obtained in step b) in order to determine if, on the processed image, the gap between the sampling tool and its projected image is equal to zero, d) if the gap between the sampling tool and its projected image is not equal to zero, displacing the sampling tool towards the reference surface and/or the reference surface towards the sampling tool and repeating steps a), b), c) and d) until said gap is equal to zero.

"Steering the displacement of a sampling tool towards a reference surface and/or of a reference surface towards a sampling tool" is understood to mean, in the sense of the present invention, controlling/directing the displacement of the sampling tool towards the reference surface and/or of the reference surface towards the sampling tool. The term "steering" must be understood in the broad sense, namely as incorporating the concepts of starting and stopping the displacement, as well as those of accelerating and slowing said displacement.

In any case, the displacement of the sampling tool towards the reference surface and/or of the reference surface towards the sampling tool results in a "coming together" of the sampling tool and the reference surface.

This "coming together" can be obtained by:
- displacement of the sampling tool towards the reference surface,
- displacement of the reference surface towards the sampling tool, or
- by a simultaneous or successive displacement of the sampling tool towards the reference surface and of the reference surface towards the sampling tool.

According to a preferred embodiment, said "coming together" results from displacement of the sampling tool towards the reference surface.

When, on the processed image obtained in step c) above, the gap between the sampling tool and its projected image is equal to zero, this means that the contact position has been reached, namely that the sampling tool and the reference surface are in contact.

The reference surface may be substantially—or even totally—flat, for example when it is a liquid medium. Alternatively, this reference surface may comprise bulges, such as raised areas (protuberances). These raised areas may, for example, correspond to bacterial colonies which have grown on the surface of an agar.

The method according to the invention preferably comprises the following additional steps:
a') illuminating the reference surface without the sampling tool in the field,
b') acquiring an image of said reference surface without the sampling tool in the field, in order to obtain a reference image;
and wherein the image processing step c) comprises the subtraction of the elements which constitute the reference image from the image of both the sampling tool and its image projected onto the reference surface, in order to retain an image which substantially represents the sampling tool and its image projected onto the reference surface.

"Subtraction of the elements which constitute the reference image from the image of the sampling tool and its image projected onto the reference surface" is understood to mean all the elements of the reference image other than the image of the sampling tool and its image projected onto the reference surface.

The illumination of the sampling tool may be maintained during the displacement of the latter (continuous illumination). Alternatively, the illumination of the sampling tool may be selective, namely occurring only after each displacement of the sampling tool so as to project the sampling image onto the reference surface for each of the different positions of the sampling tool.

The method according to the invention preferably comprises the following additional step:
e) when said gap between the sampling tool and its projected image is equal to zero, displace or continue the displacement of the sampling tool and/or of the reference surface from the contact position towards a sampling position.

The sampling position must be understood as being a position suitable for sampling the biological material of interest whilst avoiding sampling possible contaminants.

According to a preferred embodiment, this sampling position is situated substantially under the reference surface.

The displacement or the continuing of the displacement of the sampling tool and/or of the reference surface from the contact position towards a sampling position is particularly desirable if the sampling tool must be positioned under the reference surface, for example in the case of sampling biological material in liquid medium.

According to an alternative embodiment, the method according to the invention comprises the following additional step:
e') When said gap between the sampling tool and its projected image is equal to zero, halting the displacement of the sampling tool and/or of the reference surface.

This alternative embodiment may be of benefit in particular when a low quantity of a solid or semi-solid biological material (such as a bacterial biological material on agar medium) is sampled.

Preferably, in step c) of the method according to the present invention, the gap between the sampling tool and its image projected onto the reference surface is measured on the processed image between the distal end of the sampling tool and the corresponding end of its projected image.

The distal end of the sampling tool may in particular consist of the end of a sampling tip intended to come into contact with the biological material to be sampled.

According to a particular embodiment, the displacement of the sampling tool towards the reference surface, from a first position towards a second position, and/or of the reference surface towards the sampling tool, from a first position towards a second position, is performed in at least two steps.

According to another particular embodiment, the displacement of the sampling tool and/or of the reference surface is performed at at least two different speeds. For example, a first displacement of the sampling tool and/or of the reference surface is performed at a first speed then a second displacement is performed at a second speed, said first speed being greater than said second speed.

Preferably, the displacement of the sampling tool and/or of the reference surface is controlled by a stepping motor. This enables a gradual "coming together" of the sampling tool and the reference surface.

According to a particularly preferred embodiment, the image processing step c) comprises binarisation of the image, for example a double-threshold binarisation, in order to isolate, on the processed image, the image of the sampling tool and of its projected image.

According to a preferred embodiment of the present invention, the projected image of the sampling tool on the reference surface is a reflection. This reflection is obtained by reflecting the image of the sampling tool onto the reference surface (mirror effect). The reflection of the sampling tool may in particular be obtained on clear and opaque agars, under diffuse illuminations.

According to another preferred embodiment, the projected image of the sampling tool on the reference surface is a shadow, namely the shadow of the sampling tool on said reference surface. In order to generate this shadow projected onto the reference surface, the sampling tool is preferably illuminated with a light source equipped with a polariser.

The sampling tool is preferably illuminated with a light source emitting a light beam, said light beam being inclined at a Brewster's angle relative to the reference surface.

The sampling tool is preferably illuminated with an LED light source, which is, for example, white in colour.

The subject of the present invention is also a device for implementing the method according to the invention, wherein the device comprises:
- a sampling tool suitable for sampling biological material on a reference surface, such as the surface of an agar medium,
- an illuminating means for making the sampling tool visible and projecting an image of the sampling tool onto the reference surface,
- an image acquisition means such as a camera, which makes it possible to acquire an image of both the sampling tool and its image projected onto the reference surface,
- an image processing means which makes it possible to process the image and determine if, on the processed image, the gap between the sampling tool and its projected image is equal to zero,
- a displacement means, such as a motor, which makes it possible to displace the sampling tool towards the reference surface and/or the reference surface towards the sampling tool, and
- a control means suitable for controlling the displacement of the sampling tool towards the reference surface and/or of the reference surface towards the sampling tool when, on said processed image, the gap between the sampling tool and its projected image is not equal to zero.

The above-mentioned control means is suitable for controlling/steering the displacement of the sampling tool towards the reference surface and/or of the reference surface towards the sampling tool. The displacement itself will actually be carried out by the abovementioned displacement means.

Preferably, the control means is equipped with a memory for storing a gap between the sampling tool and its projected image equal to zero, said control means being suitable for controlling the displacement of said sampling tool towards said reference surface and/or of said reference surface towards said sampling tool until a gap equal to zero between the sampling tool and its projected image is obtained on said processed image.

Another object of the present invention relates to an apparatus for sampling biological material comprising the device according to the invention.

The invention shall become more clearly apparent upon reading the following description with reference to the corresponding figures which depict, by way of non-limiting example, a method and a device according to the present invention. More precisely.

Figure 1:
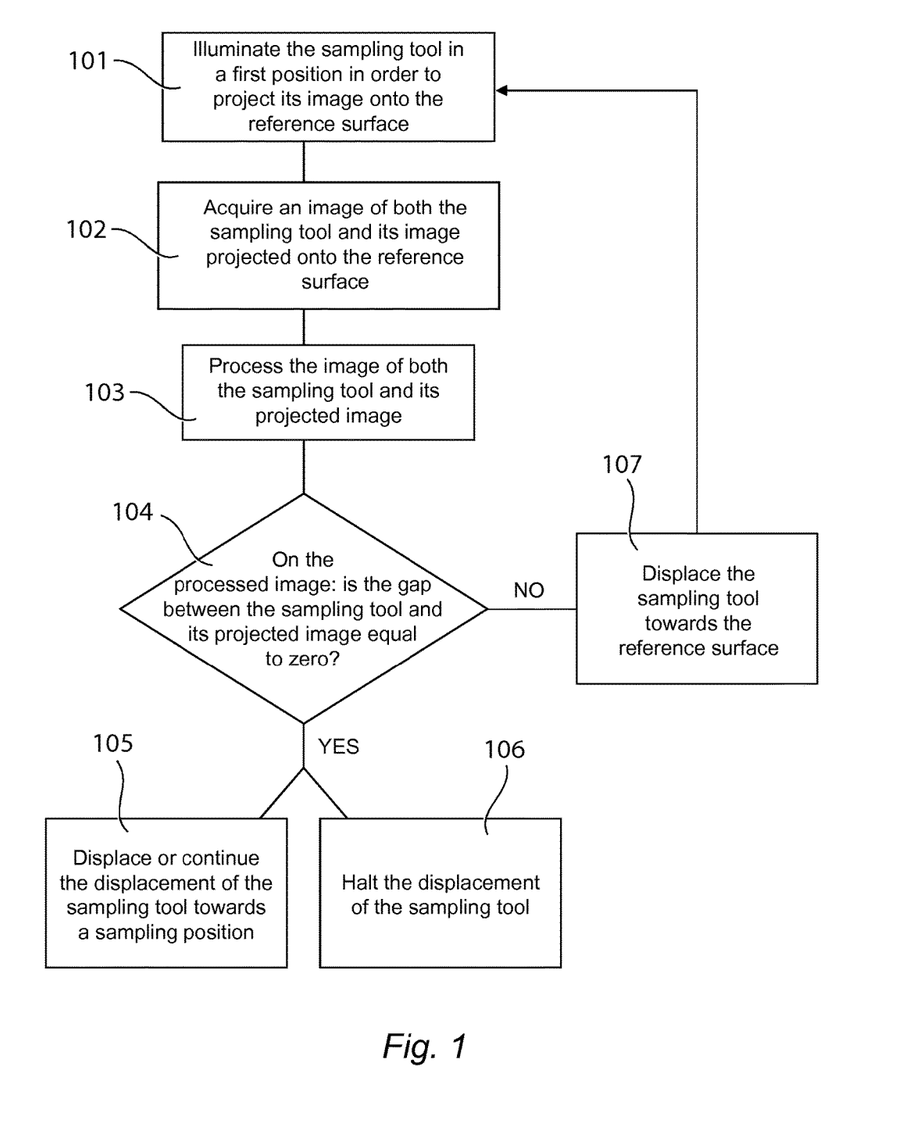
FIG. 1 shows the different steps of a first embodiment of a method of steering the displacement of a sampling tool towards a reference surface according to the invention.

The different steps of a first embodiment of the method according to the present invention are depicted in FIG. 1. The first step 101 consists in illuminating the sampling tool in a first position in order to make the sampling tool visible and project an image of the sampling tool onto the reference surface, the latter being a Petri dish, for example. The image thus obtained is called the "projected image". As indicated previously, the projected image may be a shadow obtained under collimated illumination (illumination constituted by a beam of parallel light rays) or at a reflection obtained under diffuse illumination.

Once the sampling tool is illuminated—and therefore visible—to create this image projected onto the reference surface, an image of both the sampling tool and its image projected onto the reference surface is acquired in step 102. This image is, for example, obtained using a suitable image acquisition means, such as a camera.

According to the invention, the image obtained in step 102 is then processed/analysed in step 103, preferably by a binarisation of the image, for example a double-threshold binarisation, in order to isolate, on the processed image, the image of the sampling tool and of its projected image.

Step 104 consists in verifying if, on the image processed in step 103, the gap between the sampling tool and its projected image is equal to zero (distance nil or not nil).

If this gap is equal to zero, the contact position has been reached. In this scenario, according to the user's requirements and the sampling conditions (for example the type of medium, solid medium, liquid medium, etc.):
- the sampling tool is displaced or its displacement is continued towards a sampling position in step 105; or
- the displacement of the sampling tool is halted in step 106.

On the other hand, if, in step 104, the gap between the sampling tool and its projected image is not equal to zero, this means that the contact position has not been reached, and the sampling tool is displaced towards the reference surface in step 107, then the steps 101, 102, 103 and 104 are repeated until, on the image processed in step 103, the above-mentioned gap is equal to zero, which means that the sampling tool and the reference surface are in contact (contact position).

Figure 2:
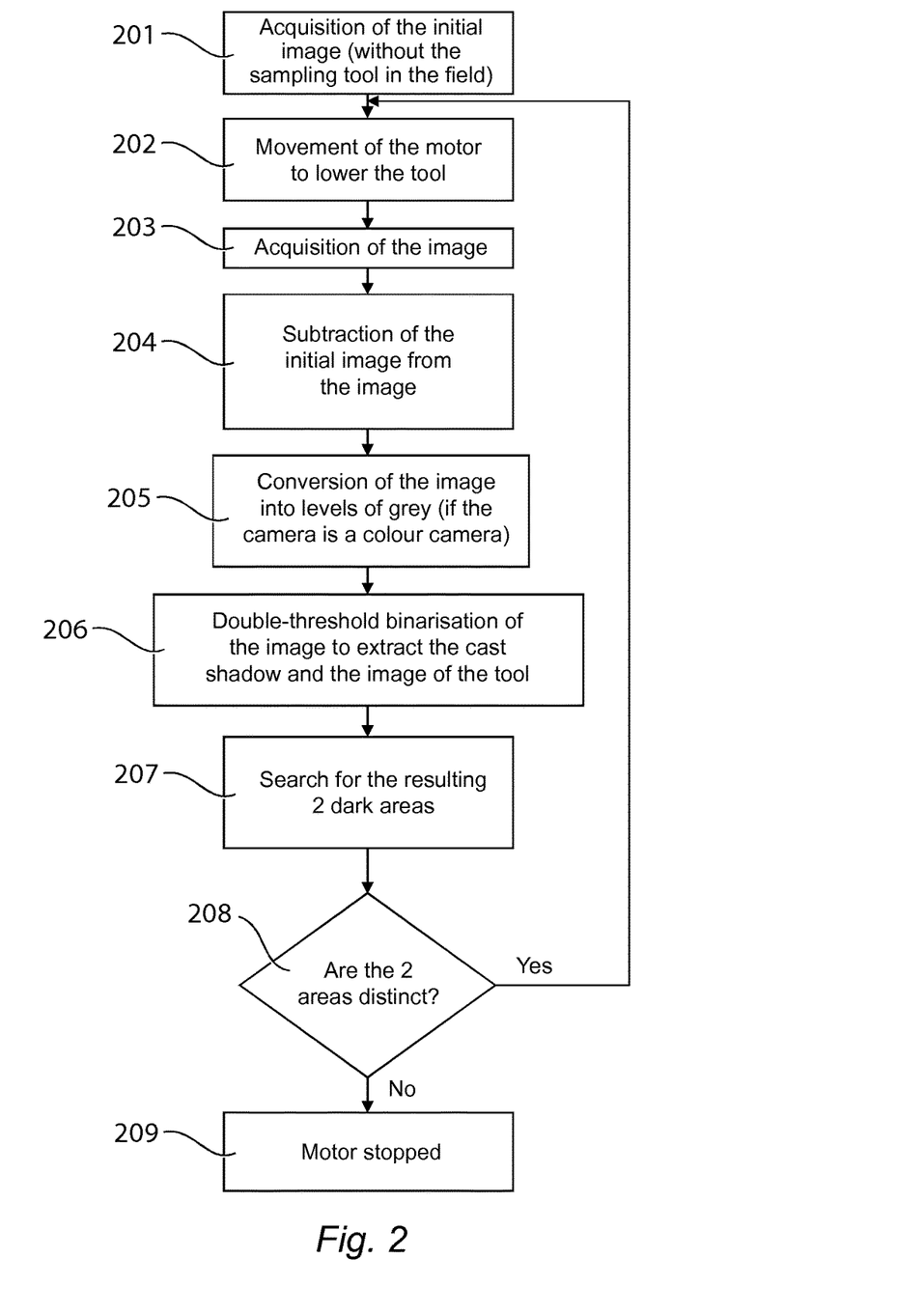
FIG. 2 depicts a second embodiment of a method which makes it possible to steer the displacement of a sampling tool towards a reference surface according to the invention, FIG. 3 schematically shows the different elements of a device suitable for steering the displacement of a sampling tool towards a reference surface; the sampling tool being positioned in a first position relative to the reference surface, FIG. 4 schematically depicts the device according to FIG. 3, wherein the sampling tool is positioned in a second position (contact position) relative to the reference surface, FIG. 5 schematically shows the image obtained by means of an image acquisition means such as a camera, after image subtraction and binarisation; the sampling tool being positioned relative to the reference surface as shown in FIG. 3.

A second embodiment of the method according to the invention is depicted in FIG. 2. In this embodiment, the image of the sampling tool projected onto the reference surface is a shadow. Evidently, this second embodiment could be suitable for a reflection-type projected image.

An image acquisition of the field in which the sampling tool is used is performed during a first step 201. This reference image is acquired in the absence of the sampling tool, namely without the sampling tool being present in the field. Said image may be used subsequently in the present method, during the image subtraction step 204 (as part of the image processing process; see below).

After acquisition of the initial image, the sampling tool is brought into the field of the image acquisition means (for example a camera). More precisely, a motor (preferably a stepping motor) is used to lower the tool in step 202 and to enable it to enter the field of the image acquisition means. When the sampling tool has entered the camera field, it is illuminated. The image of the sampling tool and of its shadow on the reference surface is acquired in step 203.

In step 204, the reference image obtained in step 201 is subtracted from the image acquired in step 203, in order to view on the resulting image only the sampling tool and the shadow it casts.

After this first image processing step, the image thus obtained (resulting image) is converted into levels of grey if the camera is a colour camera. This conversion is described in step 205.

This "subtraction" image processing operation makes it possible to obtain a resulting image containing only the image of the sampling tool and of its image projected onto the reference surface. In order to obtain this result, this subtraction operation consists, according to one preferred embodiment, of comparing each level of grey of each pixel of the acquired image with the level of grey of the corresponding pixel in the reference image. There are 255 levels of grey. If the levels of grey of these pixels are identical, the level of grey of the pixel in the resulting image will be equal to 255 (the level corresponding to the colour white); if the levels of grey of these pixels are different, the level of grey of the pixel in the resulting image shall be equal to zero (the level corresponding to the colour black).

Figure 5:
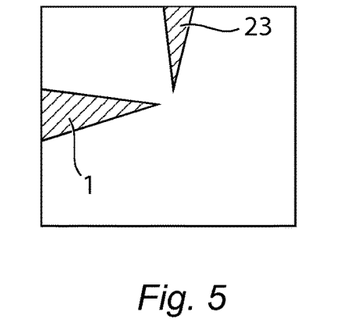
Figure 6:
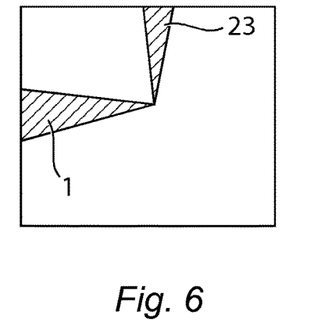
FIG. 6 depicts, again schematically, the image obtained by means of an image acquisition means such as a camera, after image subtraction and binarisation; the sampling tool being positioned relative to the reference surface as shown in FIG. 4.

The following step 206 of the image processing process consists in double-threshold binarisation, high and low, of the image in order to extract the image of the sampling tool and of the shadow it casts. The thus binarised image makes it possible to clearly distinguish the image of the sampling tool and of the shadow it casts. On said binarised image, both the sampling tool and the shadow it casts appear as two dark areas, as depicted in FIGS. 5 and 6.

The following step 207 consists of an image analysis step in which the two dark areas are sought, respectively representing the sampling tool and the shadow it casts, as indicated previously. When the two dark areas are identified, a check is performed as to whether these two zones are distinct, i.e. whether there is a gap between these two areas.

If a certain gap remains between the two above-mentioned areas, steps 202 to 208 are repeated until the two dark areas are in contact with one another (there is no longer any space between these two areas). Otherwise, if the two dark areas are in contact with one another, this indicates that the sampling tool has come into contact with the reference surface. In other words, the sampling tool has arrived at its contact position. The displacement of the sampling tool in the direction of the reference surface is halted in step 209, for example by stopping the motor which drives the sampling tool. As mentioned previously, the sampling tool may be displaced from this contact position towards a sampling position (defined above) according to the user's wishes. According to one alternative, the motor is not stopped in step 209, and the displacement of the sampling tool is continued until the sampling position is reached.

Figure 3:
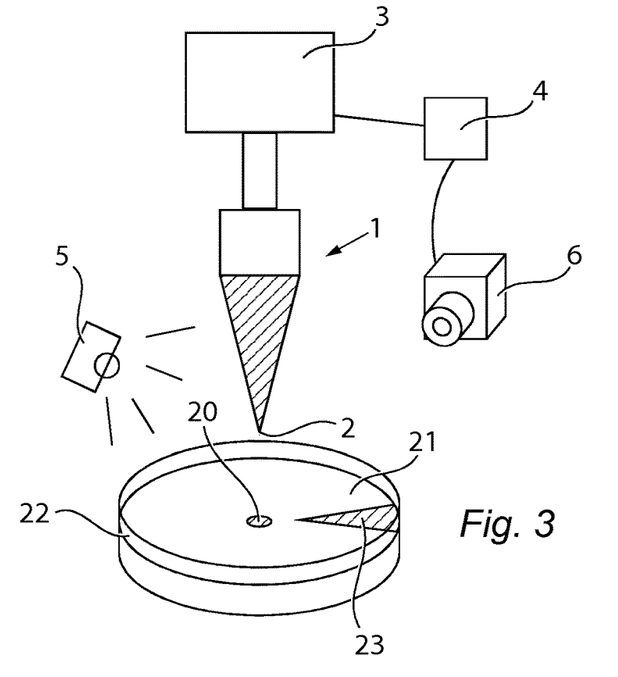

FIG. 3 schematically depicts a device which makes it possible to steer the displacement of a sampling tool towards a reference surface according to the present invention.

A sampling tool 1, which is equipped with a tip 2 intended to come into contact with a reference surface, is depicted in FIG. 3. The sampling tool 1 may be displaced from a first position towards a second position by using a motor 3, preferably a stepping motor. The motor 3 is connected to a control device 4 which controls/steers the displacement of the sampling tool 1 towards the contact position, as well as, if applicable, towards the sampling position.

As depicted in FIG. 3, the contact position of the tip 2 and the sampling tool 1 corresponds to contact between said tip 2 and a bacterial colony 20 present on an agar culture medium 21 contained in a Petri dish, the base of which is labelled 22. In the terms of the present invention, the reference surface comprises, in this configuration, the agar culture medium 21 and the bacterial colony 20.

It is important to meticulously steer the movement of the sampling tool 1 towards the bacterial colony 20 in order to sample only bacteria belonging to this bacterial colony 20, so as to avoid the previously mentioned contamination phenomena. In order to optimise the analysis of the bacterial colony 20, the sampling of bacteria belonging to this colony 20 shall preferably be performed in the contact position, in order to avoid any sampling of the agar culture medium 21. In this scenario, the contact and sampling positions are merged. Ideally, this sample shall contain only bacteria belonging to the colony 20, and no other material.

According to the invention, the displacement of the sampling tool in the direction of the reference surface is steered using a light source 5, which creates a shadow 23, also known as "cast shadow" on the reference surface.

Once the cast shadow 23 is created, a camera 6, or any other suitable image acquisition means, is used to obtain an image of the sampling tool 1 and its cast shadow 23 on the reference surface.

The image thus obtained by the camera 6 is then processed during one or more image processing steps (cf. FIG. 2, steps 204 to 206). The image thus processed is depicted in FIG. 5. In said FIG. 5 the two dark areas obtained at the end of step 206 (FIG. 2) can be seen. These two dark areas respectively represent the sampling tool 1 and its cast shadow 23 on the reference surface.

A gap between the two dark areas respectively representing the sampling tool 1 and its cast shadow 23 is visible in FIG. 5. This gap means that the tip 2 of the sampling tool 1 and the bacterial colony 20 present on the agar 21 are not in contact.

The processed image as depicted in FIG. 5 is analysed (cf. steps 207 and 208 in FIG. 2), the result of this analysis potentially generating control (steering) orders emitted by a control means 4 to the motor 3. The control means 4 may, for example, steer the lowering of the sampling tool 1 in the direction of the reference surface until the tip 2 of the sampling tool 1 is in contact with the bacterial colony 20. This contact means that the sampling tool 1 is in a contact position. As previously mentioned, this contact position may also be the sampling position in which sampling will be performed. Alternatively, the sampling position may be separate from this contact position, depending upon the nature of the biological material to be sampled, as well as the sampling medium type (solid, liquid, etc.).

Figure 4:
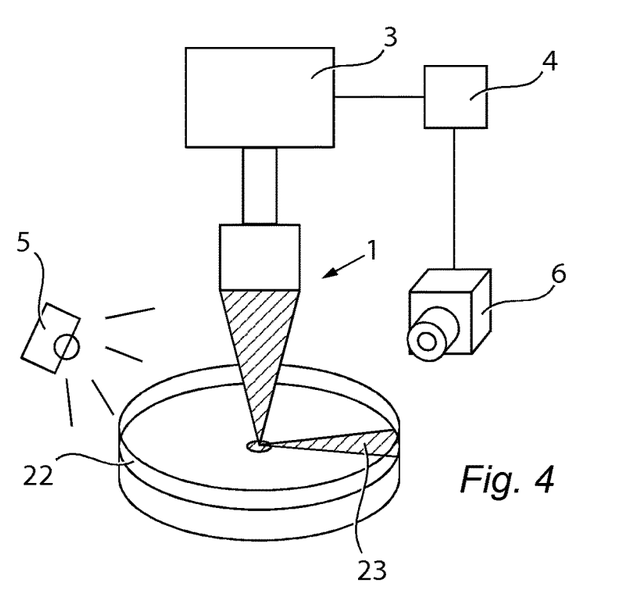

According to a preferred embodiment, the sampling tool descends in steps in the direction of the reference surface. After each step, a new image of the sampling tool 1 and of its cast shadow 23 is obtained. The control means 4 continues to instruct the motor 3 to keep lowering the sampling tool 1 until it is possible to see on the processed image that the two dark areas respectively representing the sampling tool 1 and its cast shadow 23 on the reference surface are in contact, namely that the gap between the two dark areas is zero. This situation is depicted in FIGS. 4 and 6.

Returning to FIG. 4, it clearly appears that the motor 3 has lowered the sampling tool 1 until the tip 2 is in contact with the bacterial colony 20 present on the agar culture medium 21. As mentioned previously, the sampling tool is now in a contact position, and the sampling of bacterial colonies may therefore be carried out in this contact position or in a sampling position which is distinct from the latter, depending on the user's wishes. The image of this so-called "contact" position, which is obtained by the camera 6, in step 203 and processed during the image processing steps 204 to 206, is depicted in FIG. 6.

On the processed image depicted in FIG. 6, a first dark area representing the sampling tool 1 and a second dark area representing its shadow on the reference surface (cast shadow) can be clearly seen; with the two dark areas in contact with one another. This means that the sampling tool 1 has reached its contact position, i.e. it has come into contact with the bacterial colony 20 present on the agar culture medium 21, and that its descent can therefore be halted or continued, in the same displacement or a subsequent displacement, until the sampling position is reached.

Depending upon the desired use of the sampling tool, the fact that, on the processed image, the two dark areas come into contact with one another may be an indication for the control means 4 to halt the displacement of the sampling tool 1. However, for example in the case of a sampling in liquid medium, it may be desirable for the sampling tool to continue its descent to slightly below the reference level (namely under the surface of the liquid to be sampled) to a sampling position, in order, for example, to avoid any sampling of environmental fluids, such as any sampling of ambient air.

Just as in FIG. 2, FIGS. 3, 4, 5 and 6 relate to an embodiment in which the image of the sampling tool projected onto the reference surface is a shadow. Of course, the person skilled in the art will understand that these figures could easily be adapted to the embodiment in which the projected image is a reflection.

Referring to the method and the device described above, it should be noted that, according to the present invention, a large variety of sampling tools may be used. A suitable sampling tool may consist of a "passive" sampling tool, for example a tool equipped at its end with a cotton element intended to come into contact with a bacterial colony.

Alternatively, so-called "active" sampling tools may be used, for example pipettes using the suction/discharge principle.

According to the present invention, an illumination means 5, such as a lamp, is used to illuminate the sampling tool 1 and create its cast shadow 23 on a reference surface. This illumination can be provided by one or more LEDs, for example by one or more LEDs which are white in colour. The colour of the LEDs may however vary depending on the desired uses. This type of illumination may be used to guarantee a sufficient contrast between the sampling tool 1 and its cast shadow 23.

Furthermore, the orientation of the illumination means 5 relative to the sampling tool 1 has an effect on the potential stray reflections of the light present on the reference surface.

According to one particularly preferred embodiment, and in order to promote image acquisition and to eliminate artifacts due to the stray reflection of the light source onto the reference surface, it is possible to place the illumination means 5 such that the light beam is inclined at a Brewster's angle relative to the reference surface. Furthermore, it is also recommended to use a polariser in front of the light source in order to reduce the reflections on the reference surface and, if necessary, to minimise the creation of a second cast shadow at the base of the Petri dish 22, if a translucent agar is used.

The appearance of this second shadow at the base of the Petri dish 22 may also be eliminated during the image binarisation processing step because it is less intense and offset relative to the cast shadow 23 on the reference surface.

Furthermore, it should be noted that step 206, depicted in FIG. 2, relates to double-threshold binarisation. Interestingly, a single-threshold binarisation alone is sufficient if the tip 2 of the sampling tool 1 is dark in colour, for example black.

The device for steering the displacement of a sampling tool towards a reference surface and/or of a reference surface towards the sampling tool according to the invention is, advantageously, included in a biological material sampling apparatus, which is preferably automated. This sampling apparatus will in fact preferably be an identification and/or antibiogram machine, such as a VITEK®, VITEK® 2, or VITEK® 2 Compact apparatus, or equivalent.

The invention claimed is:

1. A method of sampling biological material on a reference surface, with aid of a sampling tool, said method making it possible to steer a displacement of at least one of the sampling tool towards the reference surface and the reference surface towards the sampling tool to a contact position in which the sampling tool and the reference surface are in contact, said method comprising:
   a) illuminating the sampling tool with a light source in order to make the sampling tool visible and to project a first image of the sampling tool onto the reference surface;
   b) acquiring a second image of both the sampling tool and the projected first image of the sampling tool with a camera;
   c) processing the second image obtained in step b) in order to determine if, on the processed image, a gap between the sampling tool and the projected image of the sampling tool is equal to zero;
   d) if the gap between the sampling tool and the projected first image of the sampling tool is not equal to zero, displacing at least one of the sampling tool towards the reference surface and the reference surface towards the sampling tool and repeating steps a), b), c) and d) until said gap is equal to zero and the sampling tool and the reference surface are in said contact position; and
   e) sampling, via the sampling tool, biological material on the reference surface.

2. The method according to claim 1, comprising:
   a') illuminating the reference surface without the sampling tool in the field;
   b') acquiring a third image of said reference surface without the sampling tool in the field, in order to obtain a reference image; and
   wherein the image processing step c) comprises subtraction of elements which constitute the reference image from the second image of both the sampling tool and the projected first image of the sampling tool, in order to retain an image which substantially represents the sampling tool and the projected first image of the sampling tool.

3. The method according to claim 1, said method comprising:
d') when said gap between the sampling tool and the projected first image of the sampling tool is equal to zero, displacing or continuing the displacement of at least one of the sampling tool and the reference surface from the contact position towards a sampling position.

4. The method according to claim 1, said method comprising:
d") when said gap between the sampling tool and the projected first image of the sampling tool is equal to zero, halting the displacement of at least one of the sampling tool and the reference surface.

5. The method according to claim 1, wherein, in step c), the gap between the sampling tool and the projected first image of the sampling tool is measured on the processed image between a distal end of the sampling tool and a corresponding end of the projected first image of the sampling tool.

6. The method according to claim 1, wherein the displacement of at least one of the sampling tool towards the reference surface and the reference surface towards the sampling tool is performed in at least two steps.

7. The method according to claim 1, wherein the displacement of at least one of the sampling tool and the reference surface is performed at at least two different speeds.

8. The method according to claim 1, wherein the displacement of at least one of the sampling tool and the reference surface is controlled by a stepping motor.

9. The method according to claim 1, wherein the image processing step c) comprises binarisation of the image, in order to isolate, on the processed image, the second image of the sampling tool and the projected first image of the sampling tool.

10. The method according to claim 9, wherein binarisation of the image is a double-threshold binarisation.

11. The method according to claim 1, wherein the projected image of the sampling tool on the reference surface is a reflection.

12. The method according to claim 1, wherein the projected image of the sampling tool on the reference surface is a shadow.

13. The method according to claim 12, wherein the sampling tool is illuminated with a light source equipped with a polariser.

14. The method according to claim 12, wherein the sampling tool is illuminated with a light source emitting a light beam, said light beam being inclined at a Brewster's angle relative to the reference surface.

15. The method according to claim 12, wherein the sampling tool is illuminated with an LED light source.

* * * * *